US006784159B2

(12) United States Patent
Holub et al.

(10) Patent No.: US 6,784,159 B2
(45) Date of Patent: Aug. 31, 2004

(54) TRITERPENE SAPONINS FROM SOYBEANS FOR TREATING KIDNEY DISEASE

(75) Inventors: Bruce J. Holub, Guelph (CA); F. William Collins, Ottawa (CA); Dominique P. Bureau, Guelph (CA); Diana J. Philbrick, Guelph (CA)

(73) Assignees: Her Majesty the Queen in right of Canada, as represented by the Minister of Agriculture, Ottawa (CA); University of Guelph, Guelph (CA)

( * ) Notice: Subject to any disclaimer, the term of this patent is extended or adjusted under 35 U.S.C. 154(b) by 0 days.

(21) Appl. No.: 09/964,554

(22) Filed: Sep. 28, 2001

(65) Prior Publication Data

US 2002/0107209 A1 Aug. 8, 2002

Related U.S. Application Data

(60) Provisional application No. 60/236,341, filed on Sep. 29, 2000.

(51) Int. Cl.[7] .......................... A61K 31/704; C07J 1/00; C07H 15/24

(52) U.S. Cl. .............................. 514/26; 514/33; 536/5; 536/18.1

(58) Field of Search .................... 514/26, 33; 536/18.1, 536/5, 4; 424/48, 18 D, 75 D

(56) References Cited

U.S. PATENT DOCUMENTS 4,217,345 A * 8/1980 Shinohara et al. ............ 514/33
4,557,927 A * 12/1985 Miyake et al. ................ 424/48

FOREIGN PATENT DOCUMENTS

| | | | |
|---|---|---|---|
| WO | WO 99/34810 | * 7/1999 | .......... A61K/35/78 |
| WO | WO 99/34916 | * 7/1999 | ............ B01J/20/32 |

OTHER PUBLICATIONS

Shiraiwa et al “Composition and Structure of Group A Saponin in Saponin Seed”, Agric. Biol. Chem. 55(2), 315–322, 1991.*

Shiraiwa et al “Composition and Structure of Group A Saponin in Saponin Seed”, Agric. Biol. Chem. 55(2), 323–331, 1991.*

Shiraiwa et al “Composition and Structure of Group A Saponin in Saponin Seed”, Agric. Biol. Chem. 55(4), 911–917, 1991.*

Philbrick, Diana J. et al “Effect of a soyasaponin–enriched alcohol extract from soy protein isolate on disease progression in mice with polycystic kidney disease”, vol. 10, 1999, pp 85A.*

Shiraiwa, Masakazu, et al. Composition and Structure of “Group A Saponin” in Soybean Seed, Agric. Biol. Chem. 55(2), 315–322, 1991.

Shiraiwa, Masakazu, et al. Composition and Content of Saponins in Soybean Seed According to Variety, Cultivation Year and Maturity, Agric. Biol. Chem. 55(2), 323–331, 1991.

Shiraiwa, Masakazu et al. Compositoin and Structure of “Group B Saponin” in Soybean Seed, Agric. Biol. Chem. 55(4), 911–917, 1991.

Philbrick, DP et al., “Effect of a Soyasaponin–Enriched Alcohol Extract from Soy Protein Isolate on Disease Progression in Mice with Polycystic Kidney Disease”, American Society of Nephrology Meeting, Nov. 7, 1999.

Tomobe K et al., “Effect of Dietary Soy Protein and Genistein on Disease Progression in Mice with Polycystic Kidney Disease”, Am. J. Kidney Diseases 31:55–56, 1998.

Shiraiwa M et al., “Composition and Structure of “Group B Saponin” in Soybean Seed”, Agr. Biol. Chem. 55(4):911–917, 1991.

* cited by examiner

*Primary Examiner*—James O. Wilson
*Assistant Examiner*—Ganapathy Krishnan
(74) *Attorney, Agent, or Firm*—Bereskin & Parr

(57) ABSTRACT

A method of treating polycystic kidney disease is described. The method involves administering soyasaponin $B_b$ to an animal in need thereof.

8 Claims, 5 Drawing Sheets

TRITERPENE SAPONINS FROM SOYBEANS FOR TREATING KIDNEY DISEASE

This application claims the benefit under 35 USC §119(e) from U.S. Provisional patent application serial No. 60/236,341, filed Sep. 29, 2000.

FIELD OF THE INVENTION

The present invention relates to methods and compositions for treating kidney disease, in particular polycystic kidney disease.

BACKGROUND OF THE INVENTION

Autosomal Polycystic Kidney Disease (ADPKD) is the most prevalent, potentially fatal, inherited disease affecting the human kidney with a reported incidence of 1 out of every 500 births. It has been estimated that 500,000 persons in North America suffer from this disease of which 30,000–75,000 are Canadians. Worldwide, almost 5 million persons suffer from this debilitating disease. Polycystic kidney disease results in enlarged, cyst-filled kidneys in the abdomen producing severe, unremitting back pain, early and progressive hypertension, frequent urinary tract infections and blood in the urine. PKD also has inflammatory and other clinical components. Approximately 45% of cases can be expected to progress to end-stage renal disease (fatal) before the age of 60, adding to health care costs for dialysis treatment, hospitalization, premature morbidity due to cardiovascular and other disorders, surgeries, etc.

At present, there are no known treatments of PKD other than renal ablation, organ transplantation and cyst decompression, all costly, and sometimes life threatening. There is some evidence that, in adult humans, a slower rate of kidney deterioration is associated with a moderate protein restriction (Oldrizzi, L., et al., 1983., Kidney Int., 271:553). This therapy however, is of limited use in the growing child with PKD.

Previous studies of the inventors have shown that feeding a soy protein isolate (SPI;Supro 675 Plus HG®, Protein Technologies, International, St Louis, Mo.) markedly slowed disease progression in the DBA/2FG-pcy(pcy) mouse model of ADPKD (Tomobe K et al, 1998. Am. J. Kidney Diseases. 31:55–61). However, at that time the identity of the active component of the soy protein isolate was not determined.

In view of the foregoing, there is a need in the art to develop a treatment for polycystic kidney disease.

SUMMARY OF THE INVENTION

The present inventors have determined that soyasaponin $B_b$ is useful in treating polycystic kidney disease.

Accordingly, the present invention provides a method of treating a kidney disease comprising administering an effective amount of soyasaponin $B_b$ or an analog thereof to an animal in need thereof.

The present invention also includes pharmaceutical and nutraceutical compositions comprising an effective amount of soyasaponin $B_b$ or an analog thereof in admixture with suitable diluents or carriers.

The present invention further includes a novel method for the isolation of soyasaponin $B_b$.

Other features and advantages of the present invention will become apparent from the following detailed description. It should be understood, however, that the detailed description and the specific examples while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Use of Soyasaponin $B_b$ in Treating Kidney Disease

The present inventors have determined that supplementation of a casein-based diet with a crude saponin-enriched alcohol extract (SEAE) from a soy protein isolate (SPI) resulted in a 25% reduction in total kidney weight, a marker for disease progression in several rodent models of polycystic kidney disease (PKD). Kidney morphometric analyses showed that mean cyst volume, and hence cyst size, was significantly reduced in the kidneys from the SEAE-fed group; kidneys from animals in this group also had the lowest water content, or lowest cyst volume, a finding consistent with the inventors' observation that water is the major constituent in the cyst fluid of these diseased kidneys. Plasma creatinine and urea contents were lowest in the SEAE-fed group, which suggests that renal function in these animals had not declined to the same extent as that observed in the casein-fed mice. These beneficial effects appeared unique to the saponins derived from soybeans as supplementation of the casein-based diet with (1) ginseng (also a saponin), (2) genistein, (an isoflavone naturally present in SPI) or (3) addition of the amino acid L-arginine to the casein to mimic the amino acid composition to that of the SPI had no effect on disease progression.

The major component of the SEAE was identified as soyasaponin $B_b$ with smaller amounts of two or three unidentified saponins and trace amounts of genistein and daidzen, two naturally occurring isoflavones in soy protein. The inventors determined that the Group B soybean-derived saponins (soyasaponins), especially soyasaponin $B_b$, was an important contributor to the attenuation of cyst growth. Estimates of food intake indicated that the mice were consuming ~2.8 mg soyasaponin $B_b$/day (or 86% of the total soyasaponin intake) whereas the isoflavone intake was very small (approximately less than 22.3 mg isoflavones/day) suggesting a more limited role for these soy constituents in the retardation of disease progression.

The inventors subsequently conducted experiments with a purified soyasaponin $B_b$ concentrate and determined that soyasaponin $B_b$ had an important beneficial effect on intonation of kidney size and cyst development in the pcy mouse model of PKD. The details of the experimental protocols and results are presented in Example 1.

Accordingly, the present invention provides a method of treating a kidney disease comprising administering an effective amount of soyasaponin $B_b$ or an analog thereof to an animal in need thereof. The invention also includes the use of soyasaponin $B_b$ or an analog thereof to treat kidney disease and the use of soyasaponin $B_b$ or an analog thereof to prepare a medicament to treat kidney disease.

Figure 3:
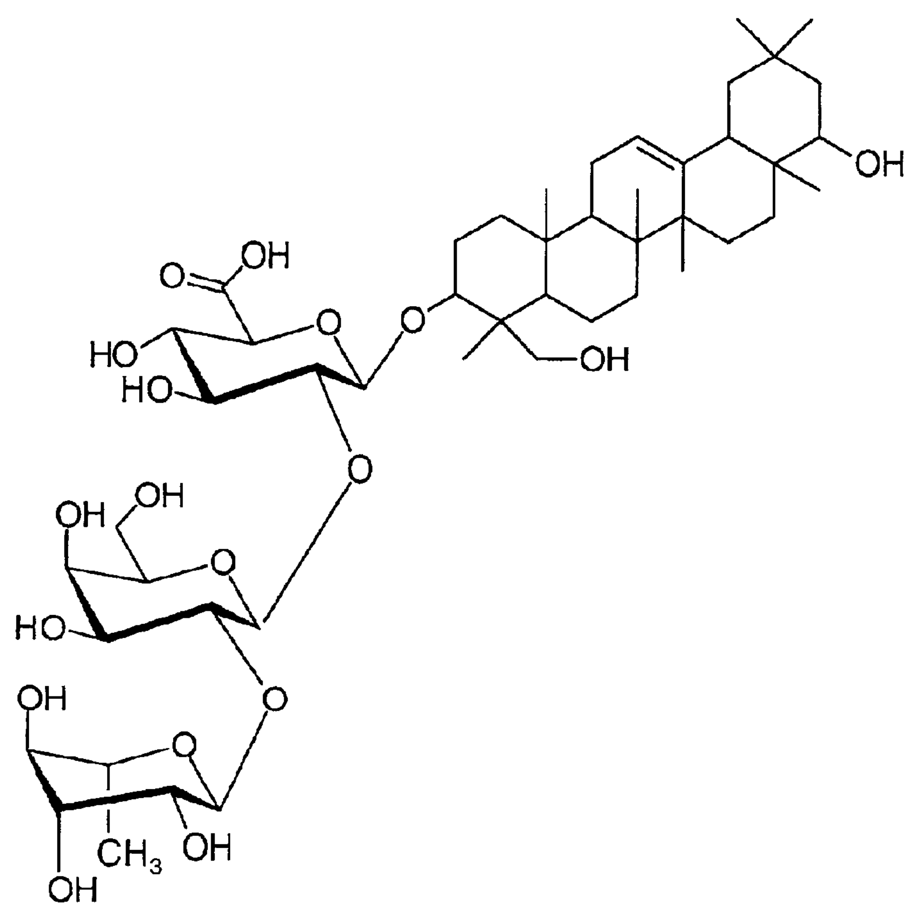
FIG. 3 shows the structure of soyasaponin $B_b$.

The term "soyasaponin $B_b$" as used herein means a saponin having the chemical formula 3-O-(α-L-rhamnosyl-1→2-β-D-galactosyl-1→2-β-D-glucuronosyl)-soyasapogenol B. The structure of soyasaponin $B_b$ is shown in FIG. 3. The soyasaponin $B_b$ may be isolated from a suitable plant source, preferably a soybean source (for example, using the method described herein or different methods) or may be chemically synthesized.

Figure 4:
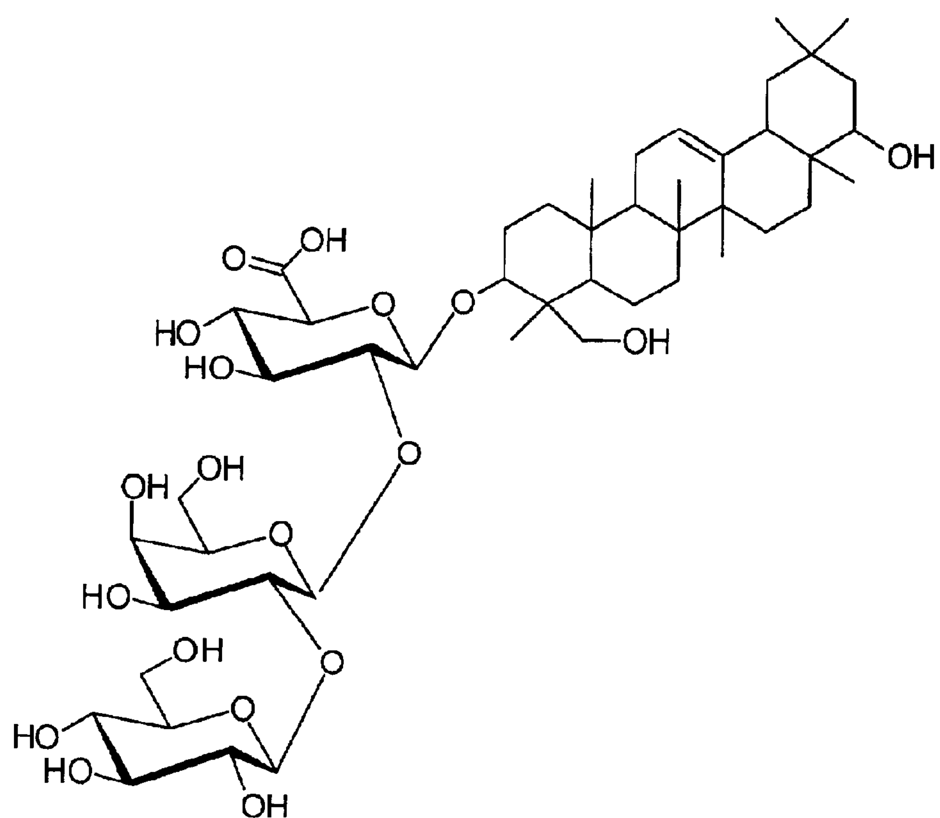
FIG. 4 shows the structure of soyasaponin $B_a$.
Figure 5:
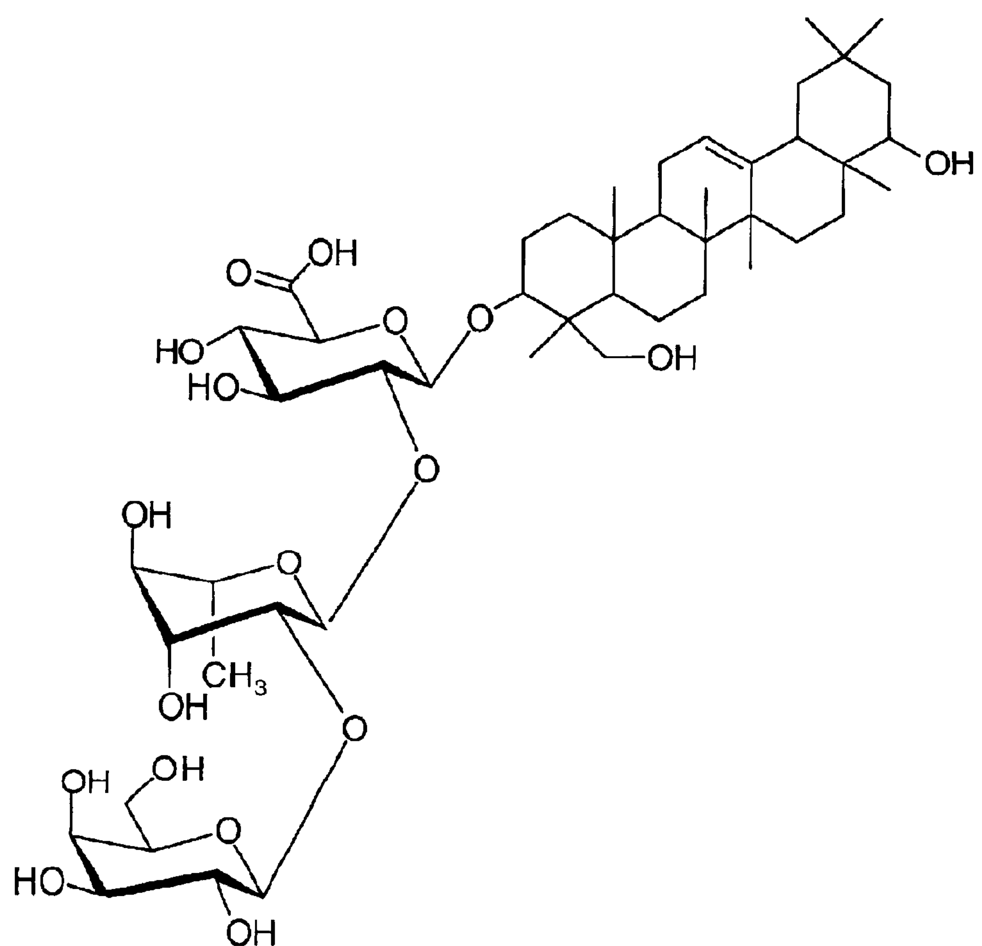
FIG. 5 shows the structure of soyasaponin $B_c$.

The term "analog" of a soyasaponin $B_b$ means a compound that is structurally related to soyasaponin $B_b$ or derived from soyasaponin $B_b$ (such as a derivative or metabolite thereof) and is useful in treating kidney disease. Examples of analogs of soyasaponin $B_b$ include compounds sharing the structural backbone of soyasaponin $B_b$ as shown in FIG. 3 including soyasaponin $B_a$ (FIG. 4) or soyasaponin $B_c$ (FIG. 5). (Shiraiwa et a., Agri. Biol. Chem., 55(4): 911–917, 1991).

The term "effective amount" as used herein means an amount effective, at dosages and for periods of time necessary to achieve the desired results.

The term "animal" as used herein includes all members of the animal kingdom, including humans. Preferably, the animal to be treated is a human.

The term "kidney disease" as used herein means any condition that affects kidney or renal function including polycystic kidney disease, acquired renal cystic disease, medullary cystic disease of the kidney, autosomal recessive polycystic kidney disease, hereditary interstitial nephritis, other inherited disorders in which PKD forms part of the symptomatology (e.g. Oral Facial Digital Syndrome), persons with a potassium-wasting disorder (Hypokalemia which also leads to renal cystic formation), glomerulonephritis and the group of renal disorders associated with inflammatory and immune disfunction in the kidney. Preferably, the kidney disease treated according to the present invention is polycystic kidney disease.

II. Compositions

The present invention also includes pharmaceutical and nutraceutical compositions comprising an effective amount of soyasaponin $B_b$ or an analog thereof in admixture with a suitable diluent or carrier.

The pharmaceutical and/or nutraceutical diluents, excipients, or carriers are suitably selected with respect to the intended form of administration, that is, oral tablets, capsules, elixirs, syrups and the like, consistent with conventional practices.

The soyasaponin $B_b$ compositions of the present invention can be administered for oral, topical, intravenous, rectal, parenteral, local, inhalant or intracerebral use. Preferably, the active substances are administered orally, for example, as a nutraceutical in the food or drink.

For example, for oral administration the active ingredients may be prepared in the form of a tablet or capsule for inclusion in the food or drink. In such a case, the active substances can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral active substances can be combined with any oral, non-toxic, pharmaceutically acceptable inert carrier such as ethanol, glycerol, water, and the like. Suitable binders, lubricants, disintegrating agents, and coloring agents can also be incorporated into the dosage form if desired or necessary. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Suitable lubricants used in these dosage forms include sodium oleate, sodium stearate, magnesium stearate, sodium benzoate, sodium acetate, sodium chloride, and the like. Examples of disintegrators include starch, methyl cellulose, agar, bentonite, xanthan gum, and the like.

Gelatin capsules may contain the active substance and powdered carriers, such as lactose, starch, cellulose derivatives, magnesium stearate, stearic acid, and the like. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract. Liquid dosage forms for oral administration may contain coloring and flavoring agents to increase acceptance.

Water, a suitable oil, saline, aqueous dextrose, and related sugar solutions and glycols such as propylene glycol or polyethylene glycols, may be used as carriers for parenteral solutions. Such solutions also preferably contain a water soluble salt of the active ingredient, suitable stabilizing agents, and if necessary, buffer substances. Suitable stabilizing agents include antioxidizing agents such as sodium bisulfate, sodium sulfite, or ascorbic acid, either alone or combined, citric acid and its salts and sodium EDTA. Parenteral solutions may also contain preservatives, such as benzalkonium chloride, methyl- or propyl-paraben, and chlorobutanol.

The soyasaponin $B_b$ can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The soyasaponin $B_b$ may also be coupled with soluble polymers which are targetable drug carriers. Examples of such polymers include polyvinylpyrrolidone, pyran copolymer, polyhydroxypropyl-methacrylamidephenol, polyhydroxyethyl-aspartamidephenol, or polyethyleneoxide-polylysine substituted with palmitoyl residues. The substances may also be coupled to biodegradable polymers useful in achieving controlled release of a drug. Suitable polymers include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Suitable pharmaceutical carriers and methods of preparing pharmaceutical dosage forms are described in Remington's Pharmaceutical Sciences, Mack Publishing Company, a standard reference text in this field.

The soyasaponin $B_b$ may be co-administered with other active ingredients that may be useful in treating PKD including other saponins such as soyasaponins $B_a$ and/or $B_c$ as well as isoflavones. In such cases the substances can be administered by any conventional means available for the use in conjunction with pharmaceuticals, either as individual separate dosage units administered simultaneously or concurrently, or in a physical combination of each component therapeutic agent in a single or combined dosage unit. The active agents can be administered alone, but are generally administered with a pharmaceutical carrier selected on the basis of the chosen route of administration and standard pharmaceutical practice as described herein.

The dose of the soyasaponin $B_b$ for use in the methods and compositions of the invention can vary depending on many factors including the weight of the subject to be treated and the status of the kidney disease. One skilled in the art can readily determine the appropriate dose in a particular case. As an example the dose of soyasaponin $B_b$ can range from 0.5 to 50 g/day, preferably 1 to 10 g/day more preferably from 0.8 to 8 g/day.

III. Method of Isolating Soyasaponin $B_b$

The present invention also includes a novel method of isolating soyasaponin $B_b$. The elucidation of the novel method arose while the inventors were seeking a pure source of soyasaponin $B_b$ for use in the above described method to treat PKD.

In order to isolate soyasaponin $B_b$ a suitable source of soybean extract enriched in saponins was sought. Two sources, both representing a processing byproduct stream from the production of protein isolates and protein concentrates as currently practised by the industry and known generically as "soy molasses" fractions were evaluated as possible starting materials. One was obtained form Central Soya (CS) and the other from Archer Daniels Midland (ADM). Both contained approximately 10 fold enrichment of total saponins over whole soybean meal and were dry, stable powders. Initially, a general procedure developed for defatted soy flour and soy hulls and described by Collins et al., 1999 (Collins F. W., Fielder, D. A., Sarr, A. B., Redmond M. J., D'Attilio, R. Z., International Patent Application WO 99/34810), was used to produce a "soysaponin subfraction" and a "soy isoflavone subfraction". However, attempts to apply this patent technology directly to the final purification of Soyasaponin $B_b$ from the soysaponin subfraction proved difficult and impractical from the standpoint of solvent usage and cost effectiveness. Surprisingly, by combining this technology with ion exchange techniques, Soyasaponin $B_b$ could be readily prepared in a pure, crystallizable form. Using this novel and improved technique, over 5 g of Soyasaponin $B_b$ were prepared and completely characterized by molecular spectroscopy.

Accordingly, the present invention provides a method of isolating soyasaponin $B_b$ from a sample comprising:

(a) solubilizing the sample in acidified aqueous alcohol, preferably 50–80% ethanol;

(b) removing polar lipids, preferably by liquid chromatography, more preferably using an Octyl Sepharose CL-4B column;

(c) solubilizing the sample from (b) in aqueous alcohol, preferably in 50–80% ethanol;

(d) passing the sample from (c) through an anion exchange column, preferably a QAE Sephadex column;

(e) eluting the sample absorbed to column in (d), preferably with an acidified aqueous alcohol, more preferably 80% ethanol with 5% formic acid; and (f) passing the sample from (e) through a preparative hydrophobic interaction chromatographic column and collecting fractions containing soyasaponin $B_b$.

The starting sample for the method will be a suitable soybean source that contains soyasaponin $B_b$. Preferably, the starting sample is a soy molasses sample derived from soy protein processing streams. The soy molasses sample is dissolved in acidified aqueous alcohol in step (a) and passed over an Octyl Sepharose CL-4B column which will retain the polar lipids. The soyasaponins will pass through the column and be dissolved again in aqueous alcohol in step (c) and passed through a QAE Sephadex anion exchange column (step (d)) where the soyasaponins will be retained by the column and subsequently eluted with an acidified aqueous alcohol (step (e)). The soyasaponins will be further purified by preparative hydrophobic chromatography (step (f), preferably on a "designer gel" such as hexadecyltrimethylammonium-substituted SP Sepharose Fast Flow as described in one of the inventor's prior application PCT/CA99/00004. In particular, the sample from step (e) will be applied to the designer gel column and eluted with 45% ethanol. The fractions containing soyasaponin $B_b$ at greater than 97% purity, as determined by HPLC-ELSD analysis, are pooled.

Preferably, the fractions containing soyasaponin $B_b$ prepared by the above method are further purified by preparative liquid chromatography, for example, on Sephadex LH-20, to obtain soyasaponin $B_b$ at greater than 99% purity. The pure soyasaponin $B_b$ can be recrystallized from hot ethanol to give colorless, fine needles of soyasaponin which can be used as described above in the methods and compositions of the invention.

The following non-limiting examples are illustrative of the present invention:

EXAMPLES

Example 1

Effect of Soyasaponin $B_b$ on Pcy Mouse Model of PKD

Figure 1:
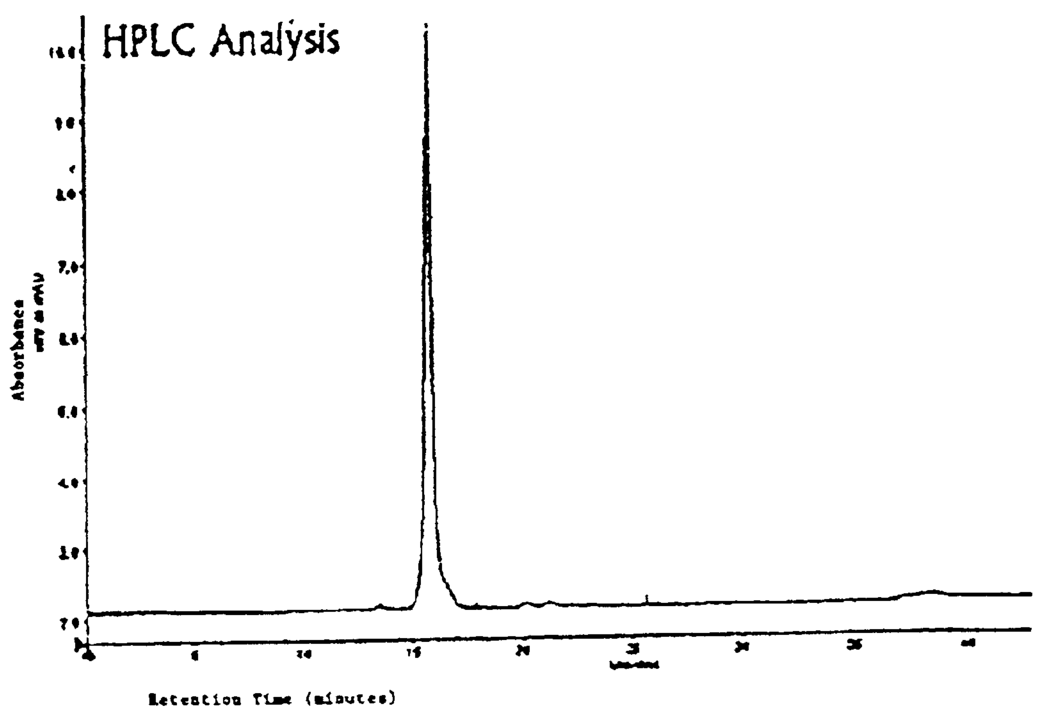
FIG. 1 is an HPLC chromatogram showing the purity of a soyasaponin $B_b$ preparation.

Experiments were conducted with a purified soyasaponin $B_b$ concentrate for a feeding trial in the pcy mice. This soysaponin $B_b$ preparation was found to be 99.5% pure as shown by the presence of a single, symmetrical peak in this HPLC trace of the $B_b$ concentrate (FIG. 1).

The feeding trial, which followed the acquisition of this soyasaponin $B_b$ concentrate, explored the possibility that this concentrate was an important contributor to the attenuation of disease progression in the pcy mouse. The protocol used in this trial involved the random assignment of young, male pcy mice to one of three dietary treatments and feeding these diets for 90 days, the usual time frame in these studies. The diets used in this feeding trial were:1) an unsupplemented casein-based diet, known to increase the severity of the renal cystic disease; 2) this casein-based diet supplemented with Novasoy 400®, a new, isoflavone-enhanced product containing low levels of the soyasaponins (ADM, Decatur, Ill.) or 3) the casein-based diet supplemented with the purified soyasaponin $B_b$ concentrate prepared by Drs. Collins and Sarr. The composition of each diet is shown in Table 1.

After three months the mice were humanely euthanized and the kidney and liver tissues removed and stored at −80 degrees Celsius until measurements of tissue water content and cell volume could be taken. Organ water content was determined in the kidney and liver by measuring the difference between the wet weight of the tissue and its subsequent weight after freeze-drying. Plasma, obtained by centrifugation of the cardiac blood, was used for standard measurements of renal function, including total protein, urea, and creatinine concentrations. Soy protein fractions enriched in the soyasaponins are reportedly hypocholesterolemic when fed to hamsters (Gatchalian-Yee M. et al. Nutrition.

13:633–639, 1997) and plasma cholesterol levels were also measured in the present experiment whenever the sample volume was adequate. Differences between treatment effects were assessed by a one-way ANOVA and the significance of these differences between means obtained by the Tukey's Honestly Significant Different Test.

The results, shown in Table 2, showed that feeding the soyasaponin $B_b$ concentrate was associated with a marked reduction in both absolute and relative kidney weight and the water content of this organ. Kidney weight in the Novasoy 400®-fed group showed a similar reduction although this group also registered an increase in the relative liver weight, not observed in the mice fed the $B_b$ concentrate. Absolute liver weight and liver water content did not differ among the casein, the Novasoy 400® and the soyasaponin $B_b$ concentrate-supplemented groups. The absence of any effect on liver weight by the soyasaponin concentrate suggests that the action of the concentrate may have been directed specifically toward the kidney in the pcy mice.

Figure 2:
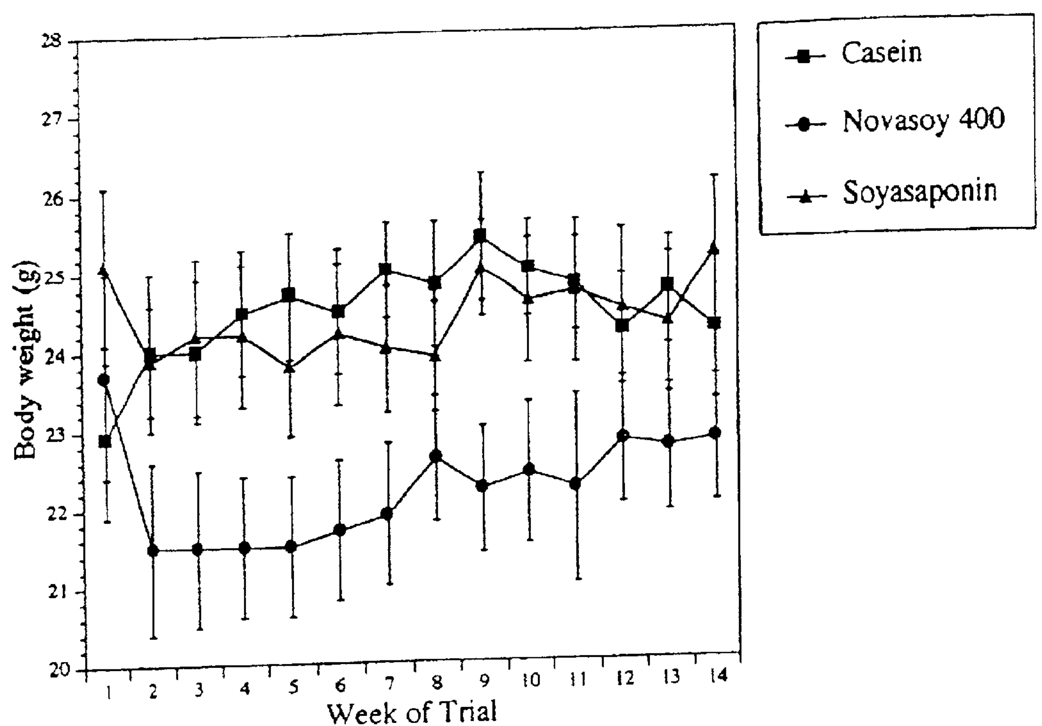
FIG. 2 is a graph showing body weight of pcy mice fed an unsupplemented casein-based diet or a diet supplemented with either Novasoy-400® or the soyasaponin $B_b$ concentrate.

No differences in final body weight were observed due to the wide variations in this measurement among the three groups. However, as shown in FIG. 2, pcy mice fed the Novasoy 400®-based diet had the slowest growth of the three groups. The diminished growth rate in this group could not be attributed to the daily food intake which was similar for all three groups (3.3±0.0, 3.9±0.0, and 3.3±0.0 g/day for the unsupplemented casein, Novasoy 400® and soyasaponin $B_b$ concentrate, respectively). Further, the estimated total Group B soyasaponin intake in the Novasoy-400 fed mice was 3.9+/−0.1 mg/day, of which 2.9 mg (or 75%) was soyasaponin B; mice fed this diet also consumed approximately 35.0+/−0.5 mg/day of daidzen and genistin. On the other hand, the amount of soyasaponin B consumed by the mice fed the pure saponin preparation was nearly twice the amount eaten by the Novasoy 400-fed group (5.9+/−0.0 versus 2.9+/−0.0 mg/day, respectively". These observations require further examination in any future trial using the Novasoy-400® as a supplement.

As shown in Table 3, plasma creatinine levels were markedly reduced in the Novasoy 400® and the $B_b$ concentrate-fed groups, suggesting a better retention of kidney function in these animals compared to those fed the unsupplemented casein diet. However, plasma cholesterol levels were markedly reduced only in the Novasoy 400®-fed group, an indication that the soyasaponin $B_b$ concentrate may have had a lesser hypocholesterolemic effect than the Novasoy 400®. There were no significant differences between the plasma urea and total protein levels among the three groups, possibly due to the length of the feeding trial.

In summary, these results indicate that a soyasaponin $B_b$ concentrate has a marked beneficial effect on attenuation of kidney size and cyst development in the pcy mouse model of PKD. The beneficial effects of this concentrate on disease progression, although similar to those observed when Novasoy 400® was fed, could be considered as a more effective therapy since they occurred in the absence of systemic effects, including growth attenuation.

Example 2

Isolation of Soyasaponin $B_b$ for Feeding Trials

For the large scale isolation of approximately 5.0 g of Soyasaponin $B_b$ two sources were used. Both are derived from soy protein processing streams and are known as the "molasses" fraction. One was a sample of NOVASOY® 400 (ADM, Decator Ill., USA) provided by Dr. B. Holub, and the other was a prototype "soy molasses" fraction provided by Dr. J. Endres, (Central Soya, Fort Wayne, Ind., USA). Both were received as a yellowish-orange free-flowing powder, and both contained at least 2% Soyasaponin $B_b$ on analysis by HPLC-ELSD. However, the composition of these two sources was considerably different with respect to the other components present and isolation of Soyasaponin $B_b$ required some slight variation in procedures. For example, the Central Soya sample contained considerable protein-like material, which was resistant to solubilization and resulted in "protein-hazes" which interfered with separations. The ADM sample contained high soluble ash content resulting in the formation of Soyasaponin $B_b$ alkali salt complexes and unpredictable solubilities (e.g. the Ca salts of Soyasaponin $B_b$ are insoluble in most solvents). This resulted in unacceptably poor recovery of pure Soyasaponin $B_b$. Consequently, an isolation strategy for each source was developed as required. In addition, since no initial source of standard Soyasaponin $B_b$ was available, preliminary methods development was difficult.

The overall isolation procedure required 5 basic steps as briefly outlined below:

1. Solubilizing the saponin in acidified aqueous alcohol (e.g. 50–80% EtOH) and removing any polar lipids by preparative liquid chromatography on Octyl Sepharaose CL-4B. In this step, all the Soyasaponins, amongst other components, pass through the column and the polar lipids amongst others, are absorbed.
2. Since the target contains a glucuronic acid moiety (also the case for Soysaponins $B_a$ and $B_c$) it will be anionic at neutral pH and will be retained on anionic exchange media. Thus, the eluate from Step 1 was concentrated, in vacuo at 40° C., dissolved in aqueous alcohol (e.g. 50–80% EtOH) and passed through an anion exchange column (such as QAE Sephadex A-25 in the formate form). The material absorbed by the column including the Soyasaponin $B_b$ was recovered by eluting the column with acidified aqueous alcohol (e.g. 80% EtOH containing 5% formic acid).
3. The target Soyasaponin $B_b$ was found to exhibit differential affinity for selected linear alkane-type hydrophobic ligands relative to both the accompanying Soyasaponins, Soysaponins $B_a$ and $B_c$ and other components present in the fraction prepared in Step 2. Therefore it could be further purified by preparative hydrophobic interaction chromatography on "Designer Gels" such as hexadecyltrimethylammonium-substituted SP Sepharose Fast-Flow (Collins et al., 1999, PCT/CA99/00004). Thus the fraction was subjected to preparative liquid chromatography on the above "Designer Gel" using aqueous alcohol (typically 45% EtOH) and the fractions containing Soyasaponin $B_b$ at higher than 97% purity (as determined by HPLC-ELSD analysis) were pooled.
4. Residual coloration of the purified Soyasaponin $B_b$ fraction prepared in Step 3 (due to cumulative solvent handling impurities amongst others) and other impurities were removed by preparative liquid chromatography on Sephadex LH-200, to give a final purified Soyasaponin $B_b$ fraction at greater than 99% purity (as determined by HPLC-ELSD analysis).

5. Finally, the Soyasaponin $B_b$ fraction prepared in Step 4 was recrystallized from hot aqueous EtOH to give colorless, fine needles of Soyasaponin $B_b$ delivered and used to prepare feeding trial diets.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Diet Composition

| Ingredient | Casein | Casein + Novasoy 400 ® | Casein + Soyasaponin $B_b$ |
|---|---|---|---|
| | (Weight % of the Total Diet) | | |
| Casein protein | 15<br>15 | 15 | |
| Vitamins + amino acids | 1.2 | 1.2 | 1.2 |
| Salts + salt supplement | 5.5 | 5.5 | 5.5 |
| Corn oil | 15 | 15 | 15 |
| Antioxidant | 0.05 | 0.05 | 0.05 |
| Sucrose + cornstarch | 60.8 | 60.8 | 60.8 |
| Fibre | 2.45 | 0.5 | 2.3 |
| Novasoy 400 ® | — | 2 | — |
| Bb concentrate | — | — | 0.18 |
| Totals | 100 | 100.1 | 100 |

Note about these diets:
1) The amount of the soyasaponin $B_b$ concentrate was based on the analyses of a saponin-rich alcohol extract (SEAE) used in a previous experiment. This crude extract was found to contain 181 mg soyasaponin $B_b$/mg extract; addition of the purified soyasaponin $B_b$ concentrate at a level of 0.18% of the total diet would provide a similar dietary intake provided by the SEAE.
2) The Novasoy 400 ® was used as the source of the purified soyasaponin $B_b$ concentrate and was added to the casein-based diet at a level (2% of the total diet) which would give equivalent amounts of the Group B soyasaponins as that provided by the concentrate.
3) The three diets contained the same amounts of food energy and protein.

TABLE 2

Body and tissue weight in pcy mice fed a unsupplemented casein-based diet or this diet supplemented with Novasoy 400 ® or the soyasaponin $B_b$ concentrate

| | Treatment | | |
|---|---|---|---|
| Measurement | Casein | Casein + Novasoy 400 ® | Casein + Soyasaponin $B_b$ |
| Total kidney wt (g) | 1.8 ± 0.1 | 1.3 ± 0.1* | 1.3 ± 0.1* |
| Total kidney wt (g/100 g body wt) | 7.0 ± 0.3 | 5.4 ± 0.3* | 5.2 ± 0.3* |
| Kidney water content (g/left kidney) | 0.82 ± 0.1 | 0.63 ± 0.1* | 0.61 ± 0.1* |
| Final body wt (g) | 25.2 ± 0.9 | 23.3 ± 0.8 | 25.1 ± 0.1 |
| Liver wt (g) | 1.2 ± 0.1 | 1.3 ± 0.1 | 1.2 ± 0.2 |
| Liver wt (g/100 g body wt) | 4.6 ± 0.1 | 5.6 ± 0.4* | 4.6 ± 0.1 |

TABLE 2-continued

Body and tissue weight in pcy mice fed a unsupplemented casein-based diet or this diet supplemented with Novasoy 400 ® or the soyasaponin $B_b$ concentrate

| | Treatment | | |
|---|---|---|---|
| Measurement | Casein | Casein + Novasoy 400 ® | Casein + Soyasaponin $B_b$ |
| Liver water content (g) | 0.84 ± 0.0 | 0.95 ± 0.1 | 0.82 ± 0.0 |

Data are averages ± standard error of the means for 8 animals/group. Values marked by asterisks (*) are significantly different ($p < 0.05$) from the casein-fed mice.

TABLE 3

Clinical Chemistries from pcy mice fed the unsupplemented casein diet or this diet supplemented with either Novasoy 400 ® or the soyasaponin Bb concentrate

| | Treatment | | |
|---|---|---|---|
| Measurement | Casein | Casein + Novasoy 400 ® | Casein + soyasaponin $B_b$ concentrate |
| Plasma creatinine (mM/L) | 30.9 ± 9.1 | 19.0 ± 2.5* | 17.5 ± 1.9* |
| Plasma cholesterol (mM/L) | 5.3 ± 0.2 | 4.3 ± 0.2* | 4.8 ± 0.3* |
| Plasma urea (mM/L) | 22.1 ± 2.3 | 15.8 ± 3.2 | 19.5 ± 3.0 |
| Plasma total protein (g/L) | 56.0 ± 1.9 | 55.7 ± 0.8 | 54.3 ± 1.1 |

Average ± standard error of the means are shown for 8 animals/group. Values marked by asterisks (*) are significantly different ($p < 0.05$) from the casein-fed mice.

We claim:

1. A method of treating polycystic kidney disease comprising administering a composition comprising an effective amount of isolated end purified soyasaponin $B_b$ as the sole active ingredient to an animal in need thereof.

2. A method according to claim 1 wherein the soyasaponin $B_b$ is given in an amount from about 1 to about 10 g/day.

3. A method of isolating soyasaponin $B_b$ from a sample comprising:

(a) solubilizing the sample in acidified aqueous alcohol;

(b) removing polar lipids by liquid chromatography;

(c) solubilizing the sample from (b) in aqueous alcohol;

(d) passing the sample from (c) through an anion exchange column;

(e) eluting the sample absorbed to column in (d) with an acidified aqueous alcohol; and (f) purifying the sample from (e) by liquid chromatography by passing the sample through a preparative hydrophobic interaction chromatographic column comprising an electrostatically-linked, aliphatic- or alicyclic-substituted anionic or cationic polysaccharide gel and collecting fractions containing soyasaponin $B_b$.

4. A method according to claim 3 wherein the starting sample is soy molasses.

5. A method according to claim 3 wherein the sample is solubilized in step (c) in 50–80% ethanol.

6. A method according to claim 3 wherein the acidified acqueous alcohol is 80% ethanol with 5% formic acid.

7. A method according to claim 3 wherein the preparative hydrophobic interaction column hexadecyltrimethylammonium-substituted SP Sepharose.

8. A method according to claim 3 wherein the soyasaponin $B_b$ isolated from step (f) is further purified by preparative liquid chromatography.

* * * * *